United States Patent
Bonrath et al.

(10) Patent No.: US 9,238,218 B2
(45) Date of Patent: Jan. 19, 2016

(54) METAL POWDERDOUS CATALYST FOR HYDROGENATION PROCESS

(71) Applicant: DSM IP ASSETS B.V., Heerlen (NL)

(72) Inventors: Werner Bonrath, Basel (CH); Axel Buss, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/380,892

(22) PCT Filed: Feb. 22, 2013

(86) PCT No.: PCT/EP2013/053512
§ 371 (c)(1),
(2) Date: Aug. 25, 2014

(87) PCT Pub. No.: WO2013/124392
PCT Pub. Date: Aug. 29, 2013

(65) Prior Publication Data
US 2015/0011791 A1  Jan. 8, 2015

(30) Foreign Application Priority Data
Feb. 24, 2012  (EP) .................................. 12156823

(51) Int. Cl.
*B01J 23/89* (2006.01)
*B01J 37/02* (2006.01)
*B01J 23/60* (2006.01)
*B01J 35/00* (2006.01)
*C07C 29/17* (2006.01)
*C07C 67/283* (2006.01)

(52) U.S. Cl.
CPC .............. *B01J 23/8993* (2013.01); *B01J 23/60* (2013.01); *B01J 35/006* (2013.01); *B01J 37/0207* (2013.01); *B01J 37/0225* (2013.01); *B01J 37/0226* (2013.01); *C07C 29/17* (2013.01); *C07C 67/283* (2013.01)

(58) Field of Classification Search
CPC .................................................... B01J 23/8993
See application file for complete search history.

(56) References Cited

U.S. PATENT DOCUMENTS

2015/0126768 A1 * 5/2015 Bonrath ........................ 560/265

FOREIGN PATENT DOCUMENTS

| WO | WO 2008/101603 | 8/2008 |
| WO | WO 2011/092280 | 8/2011 |
| WO | WO 2012/001166 | 1/2012 |

OTHER PUBLICATIONS

Semagina et al., "Structured catalyst of Pd/ZnO on sintered metal fibers for 2-methyl-3-butyn-2ol selective hydrogenation", Journal of Catalysis, vol. 251, No. 1, (Sep. 7, 2007), pp. 213-222.

* cited by examiner

*Primary Examiner* — Yong Chu
(74) *Attorney, Agent, or Firm* — Nixon & Vanderhye P.C.

(57) ABSTRACT

The present invention is related to a new metal powder catalytic system (catalyst) comprising a Fe-alloy as a carrier, its production and its use in hydrogenation processes.

16 Claims, No Drawings

METAL POWDERDOUS CATALYST FOR HYDROGENATION PROCESS

This application is the U.S. national phase of International Application No. PCT/EP2013/053512, filed on 22 Feb. 2013, which designated the U.S. and claims priority EP Application No. 12156823.2, filed on 24 Feb. 2012, the entire contents of each of which are hereby incorporated by reference.

The present invention is related to a new metal powder catalytic system (catalyst) comprising a Fe-alloy as a carrier, its production and its use in hydrogenation processes.

Powderous catalysts are well known and used in chemical reactions. Important types of such catalysts are i.e. the Lindlar catalysts.

A Lindlar catalyst is a heterogeneous catalyst which consists of palladium deposited on a calcium carbonate carrier which is also treated with various forms of lead.

Such catalysts are of such an importance that there is always a need for their improvement.

The goal of the present invention was to find a powderous catalyst with improved properties.

The powderous catalysts according to the present invention do have a metal (or metal alloy) as carrier material, instead of a calcium carbonate carrier.

This metal alloy is coated by a metal oxide layer on which palladium (Pd) is deposited.

Furthermore the new catalyst according to the present invention is free from lead (Pb).

Therefore, the present invention relates to a powderous catalytic system (I) comprising
a metal alloy carrier comprising
(i) 45 weight-% (wt-%)-75 wt-%, based on the total weight of the metal alloy, of Fe, and
(ii) 15 wt-%-30 wt-%, based on the total weight of the metal alloy, of Ni, and
(iii) 5 wt-%-20 wt-%, based on the total weight of the metal alloy, of Co, and
(iv) 3 wt-%-8 wt-%, based on the total weight of the metal alloy, of Mo, and
wherein the said metal alloy is coated by a metal oxide layer and impregnated with Pd.

It is obvious that all percentages always add up to 100.

The catalytic system is in the form of a powder.

This new catalyst has numerous advantages:
The catalyst is easy to recycle (and to remove) after the reaction. This can be done i.e. by filtration.
The catalyst can be used more than once (re-usable).
The catalyst as such is a very stable system. It is i.e. stable in regard to acids as well as to water.
The catalyst is easy to produce.
The catalyst is easy to handle.
The hydrogenation can be carried out without any solvents.
The catalyst is free from lead.
The catalyst shows high selectivity in hydrogenation reactions.

The metal alloys used are iron/nickel/cobalt/molybendum alloys. Such alloys are known as maraging steels and can be bought commercially from companies such as Matthey SA (Switzerland) and EOS GmbH (Germany). Such steels are available under the tradenames of Durnco or EOS Maraging Steel MS1.

The metal alloys can comprise further metals, such as i.e. Cu, Cr, Mn, Si, Ti, Al and/or Nb.

Furthermore the metal alloy can comprise carbon as well.

Therefore the present invention relates to a powderous catalytic system (II) comprising a metal alloy carrier comprising
(i) 60 wt-%-70 wt-%, based on the total weight of the metal alloy, of Fe, and
(ii) 15 wt-%-25 wt-%, based on the total weight of the metal alloy, of Ni, and
(iii) 5 wt-%-15 wt-%, based on the total weight of the metal alloy, of Co, and
(iv) 3.5 wt-%-7 wt-%, based on the total weight of the metal alloy, of Mo, and
wherein the said metal alloy is coated by a metal oxide layer and impregnated with Pd.

The present invention also relates to a powderous catalytic system (III), wherein catalytic system (I) or (II) comprises at least one further metal chosen from the group consisting of Cu, Cr, Mn, Si, Ti, Al and Nb.

Furthermore, the present invention also relates to a powderous catalytic system (III'), wherein the powderous catalytic system (III) comprises carbon.

Furthermore, the present invention also relates to a powderous catalytic system (III"), wherein the metal alloy of the catalytic system (I), (II), (III) or (III') is maraging steel.

The metal oxide layer, which coats the metal alloy, is non-acidic (preferably basic or amphoteric). Suitable non-acidic metal oxide layers comprise Zn, Cr, Mn, Cu or Al. Preferably the oxide layer comprise ZnO and optionally at least one further metal oxide wherein the metal is chosen from the group consisting of Cr, Mn, Mg, Cu and Al.

Therefore the present invention also relates to a powderous catalytic system (IV), wherein powderous catalytic system (I), (II), (III), (III') and/or (III") the metal oxide layer is basic or amphoteric.

Preferred is a powderous catalytic system (IV'), which is powderous catalytic system (IV), wherein the non-acidic metal oxide layer comprises Zn, Cr, Mn, Cu and/or Al (more preferably the oxide layer comprise ZnO and optionally at least one further metal oxide wherein the metal is chosen from the group consisting of Cr, Mn, Mg, Cu and Al).

Preferred is also a powderous catalytic system (IV"), which is powderous catalytic system (IV') wherein the non-acidic metal oxide layer is essentially free from Pb.

The metal alloy is preferably coated with a thin layer of ZnO (0.5-3.5 µm thickness) and optionally at least one further metal (Cr, Mn, Mg, Cu and/or Al) oxide.

Therefore the present invention also relates to a powderous catalytic system (V), which is powderous catalytic system (I), (II), (III), (III'), (III"), (IV), (IV') and/or (IV"), wherein the metal alloy is coated with a thin layer of ZnO and optionally at least one further metal (Cr, Mn, Mg, Cu and/or Al) oxide.

The coating of the metal alloy is done by commonly known processes, such as i.e. dip-coating.

Usually the catalytic system (catalyst) of the present invention comprises between 0.1 wt-% and 50 wt-%, based on the total weight of the catalyst, of ZnO, preferably between 0.1 wt-% and 30 wt-%, more preferably between 1.5 wt-% and 10 wt-% and most preferably between 2 wt-% and 8 wt-%.

Therefore the present invention also relates to a powderous catalytic system (VI), which is powderous catalytic system (I), (II), (III), (III'), (III"), (IV), (IV'), (IV") and/or (V), wherein the catalyst comprises between 0.1 wt-% and 50 wt-%, based on the total weight of the catalytic system, of ZnO (preferably between 0.1 wt-% and 30 wt-%, more preferably between 1.5 wt-% and 10 wt-% and most preferably between 2 wt-% and 8 wt-%).

In a preferred embodiment of the present invention the non-acidic metal oxide layers comprises ZnO and at least one further metal oxide wherein the metal is chosen from the group consisting of Cr, Mn, Mg, Cu and Al.

In a more preferred embodiment of the present the non-acidic metal oxide layer comprises ZnO and $Al_2O_3$.

Therefore the present invention also relates to a powderous catalytic system (VII), which is powderous catalytic system (I), (II), (III), (III'), (III"), (IV), (IV'), (IV"), (V) and/or (VI), wherein the non-acidic metal oxide layer comprises ZnO and Al$_2$O$_3$.

When a mixture of ZnO and Al$_2$O$_3$ is used then it is preferred that the ratio of ZnO:Al$_2$O$_3$ is from 2:1 to 1:2 (preferably 1:1).

Therefore the present invention also relates to a powderous catalytic system (VII'), which is powderous catalytic system (VII), wherein the ratio of ZnO:Al$_2$O$_3$ is from 2:1 to 1:2 (preferably 1:1).

The coated metal alloys are then impregnated by Pd-nanoparticles. The nanoparticles are synthesized by commonly known methods, i.e. by using PdCl$_2$ as a precursor, which is then reduced by hydrogen.

Usually the Pd-nanoparticles, which are on the non-acidic metal oxide layer, have an average particle size of between 0.5 and 20 nm, preferably of between 2 and 15 nm, more preferably of between 5 and 12 nm and most preferably of between 7 to 10 nm. (The size is measured by light scattering methods).

Therefore the present invention also relates to a powderous catalytic system (VIII), which is powderous catalytic system (I), (II), (III), (III'), (III"), (IV), (IV'), (IV"), (V), (VI), (VII) and/or (VII'), wherein the Pd-nanoparticles have an average particle size of between 0.5 and 20 nm (preferably of between 2 and 15 nm, more preferably of between 5 and 12 nm and most preferably of between 7 to 10 nm).

The catalyst according to present invention comprises between 0.001 wt-% and 5 wt-%, based on the total weight of the catalyst, of the Pd- nanoparticles, preferably between 0.01 wt-% and 2 wt-% more preferably between 0.05 wt-% and 1 wt-%.

Therefore the present invention also relates to a powderous catalytic system (IX), which is powderous catalytic system (I), (II), (III), (III'), (III"), (IV), (IV'), (IV"), (V), (VI), (VII), (VII') and/or (VIII), wherein the catalyst comprises between 0.001 wt-% and 5 wt-%, based on the total weight of the catalyst, of the Pd-nanoparticles (preferably between 0.01 wt-% and 2 wt-% more preferably between 0.05 wt-% and 1 wt-%).

The catalyst is usually activated before the use. The activation is done by using well known processes, such thermoactivation in H$_2$.

The catalyst of the present invention is used in selective catalytic hydrogenation of organic starting material, especially of organic starting material comprising a carbon-carbon triple bond, more especially of alkynol compounds.

Therefore the present invention also relates to the use of a powderous catalytic system (catalyst) (I), (II), (III), (III'), (III"), (IV), (IV'), (IV"), (V), (VI), (VII), (VII'), (VIII) and/or (IX) in selective catalytic hydrogenation of organic starting material, especially of organic starting material comprising a carbon-carbon triple bond, more especially of alkynol compounds.

Preferably the present invention relates to a process of reacting a compound of formula (I)

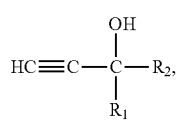
(I)

wherein
R$_1$ is linear or branched C$_5$-C$_{35}$ alkyl or linear or branched C$_5$-C$_{35}$ alkenyl moiety, wherein the C chain can be substituted, and
R$_2$ is linear or branched C$_1$-C$_4$ alkyl, wherein the C chain can be substituted,
with hydrogen in the presence of a catalyst (I), (II), (III), (III'), (III"), (IV), (IV'), (IV"), (V), (VI), (VII), (VII'), (VIII) and/or (IX)
Hydrogen is usually used in the form H$_2$ gas.
Preferred compounds of formula (I) are the following:

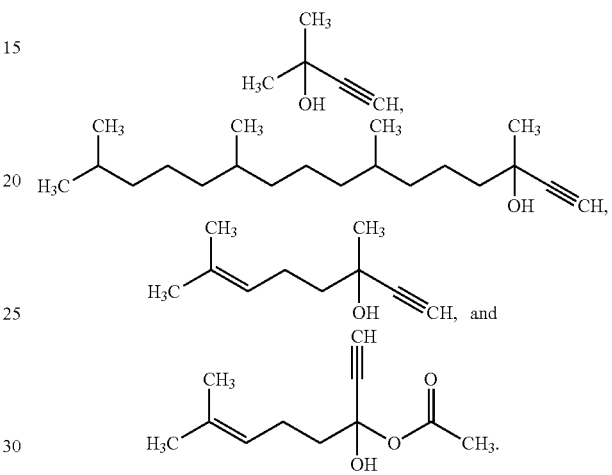

The following examples serve to illustrate the invention. All percentages are related to weight and the temperatures are given in degree Celsius, if not otherwise stated.

EXAMPLES

Example 1

Synthesis of the Catalyst (Maraging Steel Coated by Al$_2$O$_3$/ZnO and Pd Deposition)

Step 1: Thermal Pre-treatment

The stainless steel powder (EOS Maraging Steel MS1® commercially available from EOS GmbH, Germany) was subjected to a thermal pre-treatment at 450° C. for 3 h.

Step 2 Deposition of ZnO+Al$_2$O$_3$ (Coating of the Metal Alloy Carrier)

To a 100 ml-flask 20.0 g (53.3 mMol) of Al(NO$_3$)$_3$ 9H$_2$O and 70 ml of water were added. The mixture was stirred until the Al(NO$_3$)$_3$.9H$_2$O was completely dissolved. The solution was heated up to 95° C. Then 4.34 g (53.3 mMol) of ZnO powder was slowly added to the reaction solution. Heating and stirring were maintained until the ZnO was completely dissolved. The solution was then cooled down to room temperature and filtrated through a membrane filter.

The deposition of ZnO/Al$_2$O$_3$ was performed by adding the oxidized stainless steel powder (23.4 g) from step 1 to the precursor solution and stirring the mixture at room temperature for 15 min.

The powder was then filtered off via a membrane filter and dried in air at 40° C. and 125 mbar for 2 h followed by a calcination step at 450° C. for 1 h. The stirring-drying-calcination cycle was repeated 3 times. Finally, the powder support was calcined in air at 550° C. for 1 h.

22.75 g of coated maraging steel powder was obtained.

Step 3: Preparation and Deposition of the Pd-nanoparticles 318 mg (1.31 mmol) of sodium molybdate dihydrate and 212 mg (1.20 mmol) of palladium (II) chloride anhydrous were added to 60 ml of deionized water under heating (ca. 95° C.). The mixture was stirred. The heating and stirring were continued until complete evaporation of the water (solid residue was formed). Afterwards, 60 ml of deionized water were added to the residue under stirring. The evaporation-dissolving cycle was repeated two times in order to completely dissolve $PdCl_2$. Finally, 100 ml of hot water were added to the solid residue. The deep brown solution was cooled down to room temperature and filtrated through a paper filter. The filter was washed with water until the final volume of the precursor solution was 120 mL.

Afterwards the Pd° suspension was formed by bubbling hydrogen through the precursor solution for 1 h in a glass cylinder at room temperature.

The so obtained Pd° suspension and 22.75 g of the coated maraging steel powder (from step 2) were added to a 200 ml-flask. The mixture was stirred at room temperature for 15 min. The powder was filtered off via a filter paper and dried in air at 40° C. and 125 mbar for 2 h. This process was repeated twice.

Step 4: Thermo Activation of the Catalyst in $H_2$

The powder catalyst obtained from step 3 was subjected to a temperature treatment at 300° C. for 4 h under $H_2$—Ar flow. Then, it was cooled down to room temperature under the same $H_2$—Ar flow.

20.3 g of the powderous catalyst according to the present invention was obtained.

Example 2

Selective Hydrogenation of MBY to MBE

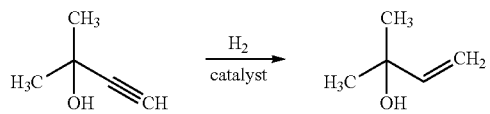

To 285 g (3.38 Mol) of MBY 1.5 g of the catalyst of Example 1 was added under stirring. The reaction was carried out at 65° C. and 4 bar pressure.

The reaction was carried out 4 times under the same conditions.

At the end of the reaction (after about 8 hours), the selectivity of the reaction was between 91.6 and 95.6% and the conversion was between 97.66 and 99.9%.

It can be seen that the new powderous catalyst has excellent properties as a catalyst for selective hydrogenations.

Example 3

Selective Hydrogenation of Dehydrolinalool (DLL)

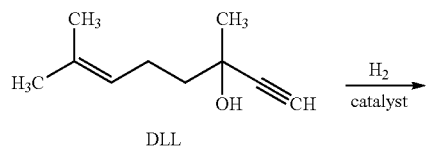

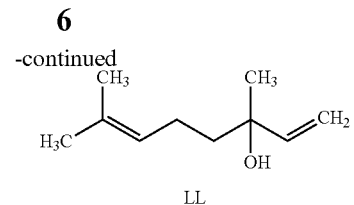

To 285 g (1.87 Mol) of DLL 1.5 g of the catalyst of Example 1 was added under stirring. The reaction was carried out at 55° C. and 4 bar pressure for about 13 hours.

At the end of the reaction the selectivity of the reaction was 84.98% and the conversion was 97.76%.

It can be seen that the new powderous catalyst has excellent properties as a catalyst for selective hydrogenations.

Example 4

Selective Hydrogenation of (DLA)

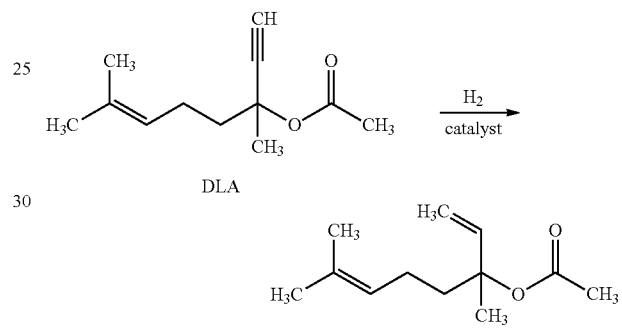

To 285 g (1.5 Mol) of DLA 1.5 g of the catalyst of Example 1 was added under stirring. The reaction was carried out at 40° C. and 4 bar pressure for about 13 hours.

At the end of the reaction the selectivity of the reaction was 87.78% and the conversion was 98.82%.

Example 5

Selective Hydrogenation of Dehydroisophytol (DIP)

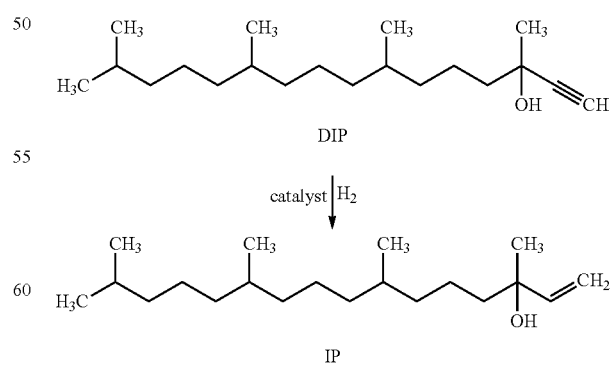

To 285 g (0.97 Mol) of DIP 1.5 g of the catalyst of Example 1 was added under stirring. The reaction was carried out at 85° C. and 4 bar pressure for about 9 hours.

At the end of the reaction the selectivity of the reaction was 81.79% and the conversion was 94.66%.

It can be seen that the new powderous catalyst has excellent properties as a catalyst for selective hydrogenations.

The invention claimed is:

1. A powderous catalytic system comprising a carrier formed of a metal alloy comprising:
   (i) 45 wt-%-75 wt-%, based on total weight of the metal alloy, of Fe,
   (ii) 15 wt-%-30 wt-%, based on total weight of the metal alloy, of Ni,
   (iii) 5 wt-%-20 wt-%, based on total weight of the metal alloy, of Co, and
   (iv) 3 wt-%-8 wt-%, based on total weight of the metal alloy, of Mo, wherein
   the metal alloy is coated by a metal oxide layer impregnated with Pd-nanoparticles.

2. The powderous catalytic system according to claim 1, wherein the metal alloy is maraging steel.

3. The powderous catalytic system according to claim 1, wherein the metal alloy comprises further metals.

4. The powderous catalytic system according to claim 1, wherein the metal alloy comprises carbon.

5. The powderous catalytic system according to claim 1, wherein the metal alloy is stainless steel comprising:
   (i) 60 wt-%-70 wt-%, based on the total weight of the metal alloy, of Fe,
   (ii) 15 wt-%-25 wt-%, based on the total weight of the metal alloy, of Ni,
   (iii) 5 wt-%-15 wt-%, based on the total weight of the metal alloy, of Co, and
   (iv) 3.5 wt-%-7 wt-%, based on the total weight of the metal alloy, of Mo.

6. The powderous catalytic system according to claim 1, wherein the metal oxide layer is basic or amphoteric.

7. The powderous catalytic system according to claim 1, wherein the metal oxide layer comprises Zn, Cr, Mn, Cu and/or Al.

8. The powderous catalytic system according to claim 1, wherein the oxide layer comprises ZnO and optionally at least one further metal oxide chosen from the group consisting of Cr, Mn, Mg, Cu and Al.

9. The powderous catalytic system according to claim 1, wherein the metal oxide layer comprises ZnO and $Al_2O_3$.

10. The powderous catalytic system according to claim 1, wherein the metal oxide layer is non-acidic, and wherein the powderous catalytic system comprises between 0.1 wt-% and 50 wt-%, based on total weight of the powderous catalytic system, of the non-acidic metal oxide layer.

11. The powderous catalytic system according to claim 1, wherein the metal oxide is mixture of ZnO and $Al_2O_3$ in a ratio of $Zn:Al_2O_3$ of 2:1 to 1:2.

12. The powderous catalytic system according to claim 1, wherein the Pd-nanoparticles have an average particle size of between 0.5 and 20 nm.

13. The powderous catalytic system according to claim 1, wherein the powderous catalytic system comprises between 0.001 wt-% and 5 wt-%, based on total weight of the powderous catalytic system, of the Pd-nanoparticles.

14. The powderous catalytic system according to claim 11, wherein the ratio of $Zn:Al_2O_3$ is 1:1.

15. A method for selective catalytic hydrogenation of an organic starting material comprising subjecting the organic starting material to catalytic hydrogenation conditions in the presence of the powderous catalytic system according to claim 1.

16. The method according to claim 15, wherein the organic starting material is a compound of formula (I):

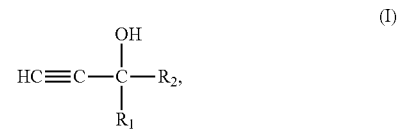

wherein
   $R_1$ is an optionally substituted linear or branched $C_5$-$C_{35}$ alkyl moiety or an optionally substituted linear or branched $C_5$-$C_{35}$ alkenyl moiety, and
   $R_2$ is an optionally substituted linear or branched $C_1$-$C_4$ alkyl moiety.

* * * * *